(12) United States Patent
Gray et al.

(10) Patent No.: US 9,829,451 B2
(45) Date of Patent: Nov. 28, 2017

(54) MICROFLUIDIC RECONFIGURATION DEVICE FOR MULTI-PLEXED SAMPLE ANALYSIS

(71) Applicant: Simon Fraser University, Burnaby (CA)

(72) Inventors: Bonnie L. Gray, Vancouver (CA); Lesley Shannon, Vancouver (CA)

(73) Assignee: Simon Fraser University, Burnaby (CA)

(*) Notice: Subject to any disclaimer, the term of this patent is extended or adjusted under 35 U.S.C. 154(b) by 0 days.

(21) Appl. No.: 14/350,034

(22) PCT Filed: Oct. 9, 2012

(86) PCT No.: PCT/CA2012/000932
§ 371 (c)(1),
(2) Date: Apr. 4, 2014

(87) PCT Pub. No.: WO2013/053039
PCT Pub. Date: Apr. 18, 2013

(65) Prior Publication Data
US 2014/0287966 A1 Sep. 25, 2014

Related U.S. Application Data

(60) Provisional application No. 61/545,192, filed on Oct. 9, 2011.

(51) Int. Cl.
*G01N 27/02* (2006.01)
*G01N 21/01* (2006.01)
(Continued)

(52) U.S. Cl.
CPC ........ *G01N 27/02* (2013.01); *B01L 3/502738* (2013.01); *F16K 99/0032* (2013.01);
(Continued)

(58) Field of Classification Search
CPC .............. B01L 2200/10; B01L 3/5027; B01L 2200/027; B01L 3/502; B01L 2200/04;
(Continued)

(56) References Cited

U.S. PATENT DOCUMENTS

2003/0159999 A1* 8/2003 Oakey et al. ............. 210/695
2009/0148933 A1* 6/2009 Battrell et al. ............ 435/287.2
(Continued)

FOREIGN PATENT DOCUMENTS

DE 10 2004 037 348 A1 3/2006

OTHER PUBLICATIONS

Man, P.F. et al., "Microfabricated Capillary-Driven Stop Value and Sample Injector," presented at the 1998 MEMS Conference, Heidelberg, Germany, Jan. 25-29, 1998, pp. 1-6.

*Primary Examiner* — Dennis M White
*Assistant Examiner* — Bryan Kilpatrick
(74) *Attorney, Agent, or Firm* — Morgan, Lewis & Bockius LLP

(57) ABSTRACT

A reconfigurable microfluidics multiplexing device for biological and chemical sample analysis which comprises: a cartridge comprising one or more sample fluid tracks (both horizontal and vertical) in a single plane, an array comprising one or more electronically programmable valves capable of being configured to alter fluid steering in the fluid tracks; a means for the array to interface with the fluid tracks; a means to control fluid flow in the fluid tracks; and a user interface to direct control of valves via control logic within the device; wherein, by the interface, valve positions are controllable and alterable.

24 Claims, 7 Drawing Sheets

(51) Int. Cl.
*F16K 99/00* (2006.01)
*H01F 1/44* (2006.01)
*B01L 3/00* (2006.01)
*G01N 27/447* (2006.01)

(52) U.S. Cl.
CPC ...... *F16K 99/0044* (2013.01); *F16K 99/0046* (2013.01); *G01N 21/01* (2013.01); *B01L 3/502* (2013.01); *B01L 3/5027* (2013.01); *B01L 3/502707* (2013.01); *B01L 2200/027* (2013.01); *B01L 2200/04* (2013.01); *B01L 2200/10* (2013.01); *B01L 2200/12* (2013.01); *B01L 2300/0819* (2013.01); *B01L 2300/0877* (2013.01); *B01L 2300/123* (2013.01); *B01L 2400/043* (2013.01); *B01L 2400/0672* (2013.01); *F16K 2099/0084* (2013.01); *G01N 27/44791* (2013.01); *H01F 1/447* (2013.01)

(58) Field of Classification Search
CPC ..... B01L 2300/0819; B01L 2300/0877; G01N 27/44791
USPC ...... 422/537, 505, 503, 502, 417, 63; 506/2, 506/39; 435/287.1
See application file for complete search history.

(56) References Cited

U.S. PATENT DOCUMENTS

2010/0112723 A1 5/2010 Battrell et al.
2011/0168269 A1 7/2011 Den Toonder et al.
2011/0214745 A1 9/2011 Zhou et al.

\* cited by examiner

FIGURE 2
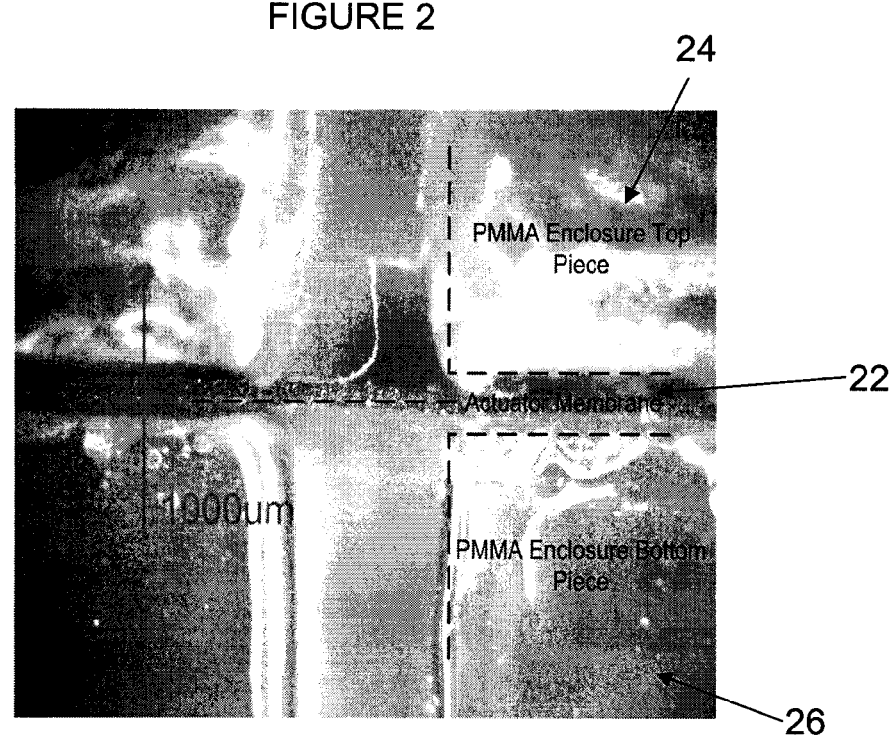
a)
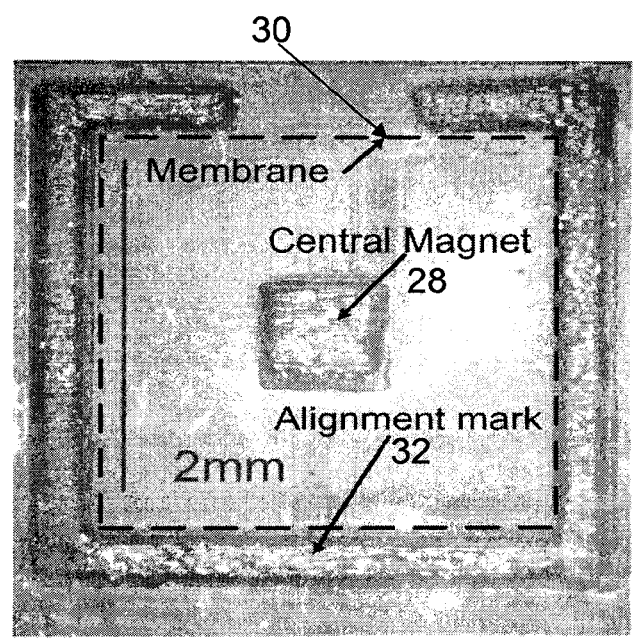
b)

MICROFLUIDIC RECONFIGURATION DEVICE FOR MULTI-PLEXED SAMPLE ANALYSIS

CROSS REFERENCE TO RELATED APPLICATION

This application is a U.S. National Phase of International Patent Application No. PCT/CA2012/000932 filed Oct. 9, 2012, which claims priority to U.S. Patent Application No. 61/545,192 filed Oct. 9, 2011, which are hereby incorporated by reference herein in their entireties.

FIELD OF THE INVENTION

The present invention relates to sample manipulation and analysis using continuous microfluidic systems.

BACKGROUND ON THE INVENTION

In many areas of importance to Canadians, including environmental monitoring, medical diagnostics, food safety, forensics, and basic biological research, the ability to perform biological and chemical agent detection is of paramount importance. There is a growing need for instruments that perform fast, accurate, and inexpensive sample manipulation and processing with high-throughput. Currently, such large scale analysis is performed using slow conventional lab techniques (e.g. microbial culture at a central laboratory) or large table-top systems. More recently, devices based on microfluidics offer possibilities for: 1) the fast manipulation and sorting of large numbers of samples, and 2) multiplexed analysis of a single sample for many different constituents—utilizing a system that is small enough to be portable or even hand-held.

Microfluidics deals with the precise control of micro- to nano-liters of fluid. The benefits of scaling chemical processes to this level include extremely low volumes of samples and reagents that can be very expensive, highly parallel processes for massive throughput, faster reaction times, and safer testing through decreased volumes of dangerous samples and reactions. Called "lab-on-a-chip" (LOC), these types of systems face a number of key challenges. When scaled to microscale fluidic channels, surface tension, capillary forces, and other fluid dynamics become major considerations. Microfluidics applications usually require external pressure sources through pumps or centrifugal force; or electrokinetics for flow. Liquids must be precisely manipulated, necessitating separate microfluidic channels (or "microfluidic tracks") for each test, resulting in a large array of permanently configured channels occupying a lot of space and limiting the number of parallel tests. Practical applications require LOCs with a plurality of independently controlled valves to achieve true LOC functionality. Furthermore, the majority of technologies thus-far employed for multiplexed fluid manipulation require large off-chip support devices (e.g., pneumatics), or are based on other technologies (e.g., electrowetting, described below) that offer promise, but have relatively strict requirements for the fluid sample manipulation and sample transfer between devices.

Following the analogy of digital microelectronics, the approach of open structures, where discrete, independently controllable droplets are manipulated on a substrate using binary electrical signals is referred to as "digital microfluidics". By using discrete unit-volume droplets, a microfluidic operation may be defined as a set of repeated basic operations, i.e., moving one unit of fluid over one unit of distance. Droplets may be formed using surface tension properties of the liquid. Actuation of a droplet is based on the presence of changing the surface tension (or wetting) of the fluid electronically, using electrical forces generated by electrodes placed beneath the bottom surface on which the droplet is located. Different types of electric forces can be used to control the shape and motion of the droplets. One technique that can be used to create the foregoing electric forces is based on the aforementioned electrowetting which relies on the dependence of the contact angle of the droplet on voltage and may utilize DC or low-frequency AC field. Droplets are placed on a surface having electrodes located beneath the surface. The shape and motion of the droplets may be controlled by switching the voltages of the electrodes. By sequentially energizing and de-energizing the electrodes in a controlled manner, one or more droplets can be moved along a path or array formation of electrodes. Detection or analysis related to processing of one or more droplets using the device is performed "on-chip" (that is on the device itself), such as using "on-chip" electrical and/or optical detection. One such technique that may be used is laser induced fluorescence (LIF) in which a droplet is moved to a location on the device and a laser beam is directed onto the droplet causing optical emissions from molecules that have been excited to higher energy levels by absorption of electromagnetic radiation. Emission of fluorescent light therefrom may be used to detect whether a particular reaction occurred. It should be noted that droplets can thus be moved, mixed, and analyzed on-chip.

In contrast to digital microfluidics is technology related to "continuous-flow microfluidics", which is based on manipulation of liquid flow through micro-fabricated channels. Actuation of liquid flow is implemented either by external pressure sources, external mechanical pumps, integrated mechanical micropumps, capillary forces, electrokinetics, or by combinations of capillary forces and electrokinetic mechanisms. Conventionally known continuous-flow devices are adequate for many well-defined and simple biochemical applications, and for certain tasks such as chemical separation, but they are less suitable for tasks requiring a high degree of flexibility or in effect fluid manipulations. These closed-channel systems are inherently difficult to integrate and scale because the parameters that govern flow field vary along the flow path making the fluid flow at any one location dependent on the properties of the entire system. Permanently etched microstructures also lead to limited reconfigurability and poor fault tolerance capability. Methods that seek to solve the reconfigurability aspects have thus far been based mainly on a type of microfluidic valving that requires a large amount of support equipment to drive arrays of, e.g., pneumatic valves, resulting in a "chip-in-lab" situation rather than a self-contained "lab-on-chip".

There remains the need for a simple, portable, versatile, easily configurable, continuous-flow device which is adaptable in in-situ and portable testing environments. It is an object of the present invention to obviate or mitigate the above challenges and disadvantages.

SUMMARY OF THE INVENTION

The present invention provides a reconfigurable microfluidics multiplexing device for biological and chemical sample analysis which comprises:
  a) a cartridge comprising one or more sample fluid tracks (both horizontal and vertical) in a single plane;

b) an array comprising one or more electronically programmable valves capable of being configured to alter fluid steering in the fluid tracks;
c) a means for the array to interface with the fluid tracks;
d) a means to control fluid flow in the fluid tracks; and
e) user interface to direct control of valves via control logic within the device;
wherein, by the interface, valves positions are controllable and alterable.

Optionally, as part of the device, there are provided multi-dimensional fluidic track switch blocks for a planar fluidic track network.

In another aspect, the invention further provides a method of analyzing fluid samples using the microfluidics multiplexing device as described and claimed herein.

In another aspect, the invention further provides a kit comprising a cartridge comprising one or more sample fluid tracks in a single plane and an array comprising one or more electronically programmable valves capable of being configured and reconfigured to alter fluid steering in the fluid tracks and a user interface to direct control of valves via control logic.

In another aspect, the invention further provides the portable use of a microfluidics multiplexing device for biological and chemical sample analysis, said device comprising:
a) a cartridge comprising one or more sample fluid tracks in a single plane;
b) an array comprising one or more electronically programmable valves capable of being configured to alter fluid steering in the fluid tracks;
c) a means for the array to interface with the fluid tracks;
d) a means to control fluid flow in the fluid tracks; and
e) user interface to direct control of valves via control logic within the device;
wherein, by the interface, valves positions are controllable and alterable.

The present invention provides, in another aspect, a computer readable medium including at least computer program code for enabling the operation of the a reconfigurable microfluidics multiplexing device as described herein.

The device of the present invention can be characterized as a "Microfluidic, Reconfigurable On-site Analyser for Multiplexed Samples" (μROAMS), which is a new approach to the high-throughput portability problem accomplished through the merging of electronically controlled functional materials for microfluidics with state-of-the-art field programmable technology. Specifically, the microfluidic multiplexing device of the present invention is based on a reconfigurable microfluidic interconnect and allows manipulation of micro- to nano-liter volumes of fluid "on-chip" in a highly versatile yet organized manner, while using less reagents and producing less waste than prior known techniques and devices.

Samples are directed within the device, similar to electrons in an integrated circuit and stored, tested, and moved off-device as desired. In operation, the control of the valves is programmed on-site to perform the needed functions via a simple user interface and a synthesis flow to convert a user's description into a "configuration bit-stream" to control the valves.

Previously known microplatforms for large scale analysis are not portable and/or are unable to support a sufficient number of samples to justify mainstream commercial acceptance. Within the scope of the present invention, there is provided a unique μROAMS with three principle architectural components: 1) a generic assembly comprising the user interface and the microvalve configuration controller; 2) a reconfigurable microfluidic array; and 3) an application specific sensor/reporter module.

Using an array of simple valves and fluid tracks, fluid can be manipulated within the device, similar to electrons in an integrated circuit, as well as stored, tested and moved off device as desired. The control valves and fluid manipulation is repeatedly reconfigurable allowing dynamic in situ programming of specific functions. A user can direct the number of samples, what tests are to be performed, what fluid samples are the be extracted, and what function the device will perform in each testing procedure etc. . . . . . In each such instance, new cartridges may be inserted tailored to a particular application (for example, water or food quality monitoring, immunoassays etc. . . . ). Importantly, using the device of the present invention, samples can undergo multiplexed analysis: single samples can be examined for large number of analytes (hence multi-plexed). Having a large array of fluid tracks in a permanent configuration (as per prior devices) takes up space and limits the number of tests that can be performed. In contrast, within the device of the present invention, the tracks or channels are not fixed but are dynamically alterable using a valve/fluid track interface.

There is a growing need for analytic devices which provide fast, accurate, and inexpensive sample manipulation with high-throughput for detection of agents from: 1) many samples; and/or 2) to detect multiple agents in a single sample. Currently, such large scale analysis is mostly performed using slow conventional lab techniques or large table-top systems. While many successful microfluidic technologies have been developed, their use in multiplexed analysis has thus far been limited due to: the large size (footprint) for multiple parallel fluid channels; technologies requiring large off-chip support such as pneumatics; or strict requirements for fluid manipulation and transfer between devices.

Within the device of the present invention, each and every one of said disadvantages is overcome: the device is designed to process small samples sizes, parallel samples can be processed and analyses are conducted. Equally importantly, the device is 100% portable.

Without limiting the general range of applications, the structure, system and method of the present invention are especially suited to immunology and drug development tests, polymerase chain reaction (PCR), blood tests, urinalysis, water (and other environmental) sample testing and food sample testing to name a few.

These and other objects and advantages of the present invention will become more apparent to those skilled in the art upon reviewing the description of the preferred embodiments of the invention, in conjunction with the figures and examples.

BRIEF DESCRIPTION OF THE DRAWINGS

The following figures set forth embodiments in which like reference numerals denote like parts. Embodiments are illustrated by way of example and not by way of limitation in all of the accompanying figures in which:

FIG. 2a is a front view of an example actuator membrane looking into the viewing window;

FIG. 2b is a top view of an example single actuator;

PREFERRED EMBODIMENTS OF THE INVENTION

Figure 1:
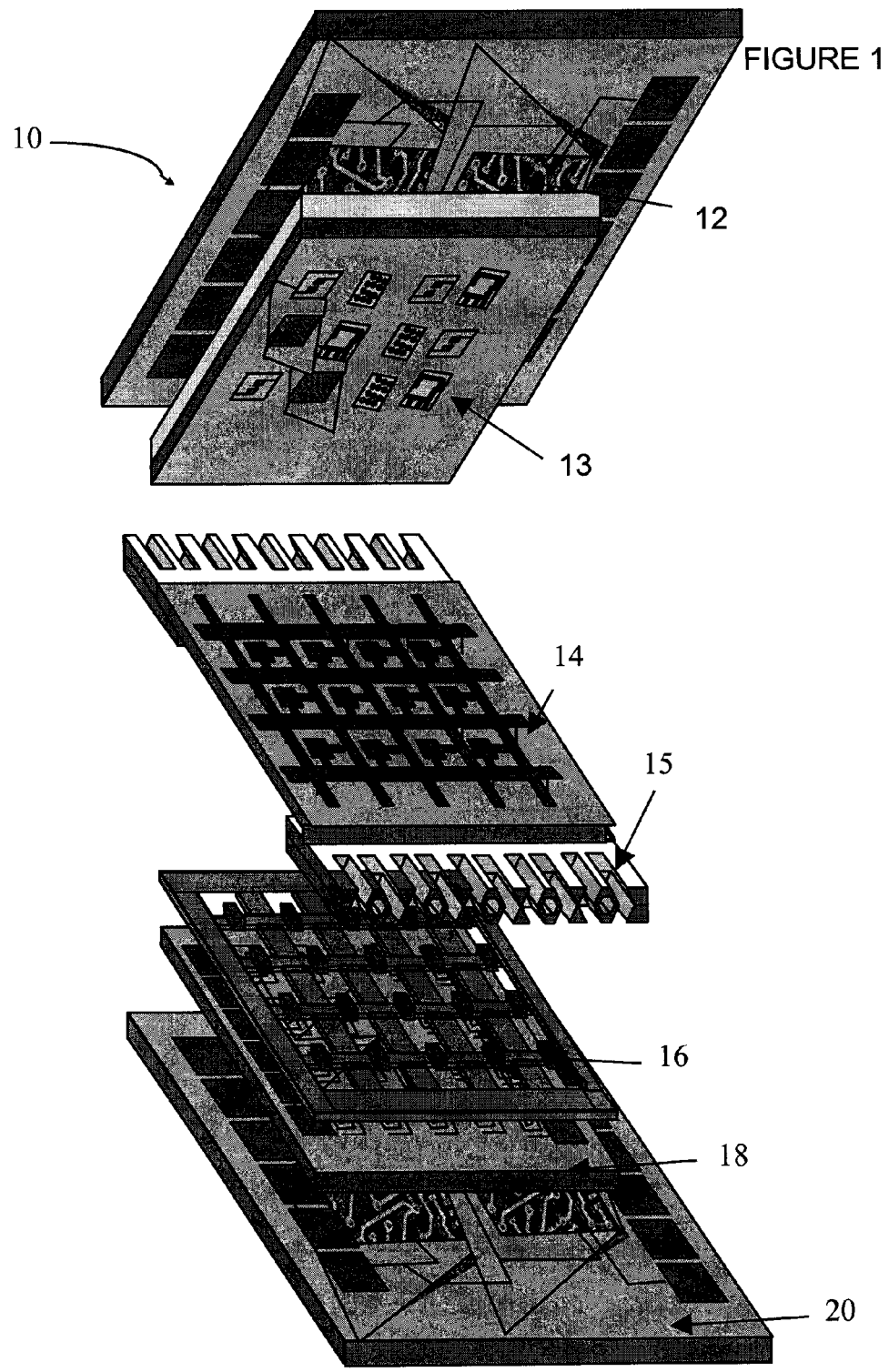
FIG. 1 is perspective view of an example μROAMS platform and a model of the reconfigurable microfluidic track network.

A detailed description of one or more embodiments of the invention is provided below along with accompanying figures that illustrate the principles of the invention. As such this detailed description illustrates the invention by way of example and not by way of limitation. The description will clearly enable one skilled in the art to make and use the invention, and describes several embodiments, adaptations, variations and alternatives and uses of the invention, including what we presently believe is the best mode for carrying out the invention. It is to be clearly understood that routine variations and adaptations can be made to the invention as described, and such variations and adaptations squarely fall within the spirit and scope of the invention.

In other words, the invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured. Similar reference characters denote similar elements throughout various views depicted in the figures.

This description of preferred embodiments is to be read in connection with the accompanying drawings, which are part of the entire written description of this invention. In the description, corresponding reference numbers are used throughout to identify the same or functionally similar elements. Relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and are not intended to require a particular orientation unless specifically stated as such. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" (if used) is such an attachment, coupling or connection that allows the pertinent structures to operate as intended by virtue of that relationship.

In the present disclosure and claims, the word "comprising" and its derivatives including "comprises" and "comprise" include each of the stated integers but does not exclude the inclusion of one or more further integers. The term track and channel may be interchanged herein.

The term "variation" of an invention means an embodiment of the invention, unless expressly specified otherwise. A reference to "another embodiment" or "another aspect" in describing an embodiment does not imply that the referenced embodiment is mutually exclusive with another embodiment (e.g., an embodiment described before the referenced embodiment), unless expressly specified otherwise.

The term "including" and variations thereof mean "including but not limited to", unless expressly specified otherwise.

The terms "a", "an" and "the" mean "one or more", unless expressly specified otherwise.

The term "plurality" means "two or more", unless expressly specified otherwise.

The term "herein" means "in the present application, including anything which may be incorporated by reference", unless expressly specified otherwise.

The term "whereby" is used herein only to precede a clause or other set of words that express only the intended result, objective or consequence of something that is previously and explicitly recited. Thus, when the term "whereby" is used in a claim, the clause or other words that the term "whereby" modifies do not establish specific further limitations of the claim or otherwise restricts the meaning or scope of the claim.

The term "e.g." and like terms mean "for example", and thus does not limit the term or phrase it explains. For example, in a sentence "the computer sends data (e.g., instructions, a data structure) over the Internet", the term "e.g." explains that "instructions" are an example of "data" that the computer may send over the Internet, and also explains that "a data structure" is an example of "data" that the computer may send over the Internet. However, both "instructions" and "a data structure" are merely examples of "data", and other things besides "instructions" and "a data structure" can be "data".

The term "respective" and like terms mean "taken individually". Thus if two or more things have "respective" characteristics, then each such thing has its own characteristic, and these characteristics can be different from each other but need not be. For example, the phrase "each of two machines has a respective function" means that the first such machine has a function and the second such machine has a function as well. The function of the first machine may or may not be the same as the function of the second machine.

The term "i.e." and like terms mean "that is", and thus limits the term or phrase it explains. For example, in the sentence "the computer sends data (i.e., instructions) over the Internet", the term "i.e." explains that "instructions" are the "data" that the computer sends over the Internet.

The term "track" as used herein is to be interpreted in a broad sense. Thus, it is not intended to be restricted to elongated configurations where the transverse or longitudinal dimension greatly exceeds the diameter or cross-sectional dimension. Rather, the term is meant to include cavities, tunnels, or chambers of any desired shape or configuration through which liquids may be directed. Such a fluid cavity may, for example, comprise a flow-through cell where fluid is to be continually passed or, alternatively, a chamber for holding a specified, discrete amount of fluid for a specified amount of time. "Tracks" may be filled or may contain internal structures comprising valves or equivalent components. Multiple tracks or a collection of tracks may be referred to as a "channel".

The term "inlet" is the passageway of fluid into a track or a channel.

The term "outlet" is the passageway of fluid out of a track or a channel.

The term "elutant" or "eluted sample" as used herein refers to a sample that is collected after processing with at least one module of the microfluidic device.

The term "computer" can refer to any apparatus that is capable of accepting a structured input, processing the structured input according to prescribed rules, and producing results of the processing as output. Examples of a computer include: a computer; a general purpose computer; a supercomputer; a mainframe; a super mini-computer; a mini-computer; a workstation; a micro-computer; a server; an interactive television; a hybrid combination of a computer and an interactive television; and application-specific hardware to emulate a computer and/or software. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

The term "computer-readable medium" may refer to any storage device used for storing data accessible by a computer, as well as any other means for providing access to data by a computer. Examples of a storage-device-type computer-readable medium include: a magnetic hard disk; a floppy disk; an optical disk, such as a CD-ROM and a DVD; a magnetic tape; a memory chip.

The term "software" can refer to prescribed rules to operate a computer. Examples of software include: software; code segments; instructions; computer programs; and programmed logic.

The term a "computer system" may refer to a system having a computer, where the computer comprises a computer-readable medium embodying software to operate the computer.

Other than in the operating examples, or where otherwise indicated, all numbers expressing quantities of ingredients or reaction conditions used herein should be understood as modified in all instances by the term "about." The term "about" when used in connection with percentages can mean+−0.1%.

This invention is further illustrated by the following examples which should not be construed as limiting. The contents of all references cited throughout this application, as well as the figures and tables are incorporated herein by reference.

Micro-Total Analysis systems (µTAS) and labs-on-a-chip (LOC) are integrated technologies that employ passive and active microfluidic devices to transport, manipulate, and analyze very small amounts of fluid for a variety of medical, environmental, and industrial applications. Such microfluidic systems may consist of various components including micromixers, tracks, valves, pumps, and interconnect structures that are combined together for a variety of microfluidics-based LOC and µTAS applications.

While microfluidic technology aims to solve portability and turn-around time problems, existing devices often employ highly specific configurations in the form of complex cartridges that limit the number of samples that can be multiplexed due to their design complexity. Other microfluidic solutions for large numbers of samples/tests require external equipment, e.g. pneumatic valving, to control the microfluidic network. Droplet-based microfluidics perform fluid manipulation via, for example, electrowetting to offer multiple-fluid-sample steering, however these systems are not without disadvantages. Fluid-track (track) based systems are best understood with a basis in conventional fluid dynamics; therefore, there are fewer problems when samples travel between modules, such task being difficult using electrowetting-based fluid transport (digital microfluidics).

Within the backdrop of these drawbacks to existing systems, the innovative µROAMS platform of the present invention was developed and refined. The present invention provides a generic, reconfigurable, on-site programmable, microfluidics device/array that can be used for sample manipulation, detection and analysis in a wide variety of applications ranging from point-of-care medicine to a range of environmental and natural resource applications.

The present invention preferably comprises a valve manifold that can be reconfigured on an on-going basis by a compute platform (for example, an FPGA), to result in an efficient initial configuration that is further able to dynamically adapt to changes based on user inputs and microreactor results at runtime. Using the device, multiple tests can be provided for multiple samples. External equipment (for example pneumatic valves, are not required between the compute platform and the multiplexer.

The device/array is portable for use in field applications and highly usable due to the architecture. Within the scope of one preferred aspect of the present invention the concept of field-programmable silicon-based technology (FPGAs) has been modified and transferred to the world of microfluidics. In one aspect, an array of sample wells arranged in a two dimensional grid is interconnected through programmable valves (analogous to FPGA switches) that are used to connect "fluidic-tracks" (akin to FPGA wire segments) to "route" fluidic samples to and from their desired locations. This provides a user-friendly and portable device that can be user-configured to support the testing, detection and sampling protocols dictated by the available sensor-types on multiple samples. It is to be fully understood that the present application is not limited to FPGA like devices. In fact, other computing platforms are equally applicable and usable.

The prevent invention, in one aspect, provides a dynamically reconfigurable microfluidics multiplexing device for biological and chemical sample analysis which comprises:
  a) a cartridge comprising one or more sample fluid tracks in a single plane;
  b) an array comprising one or more electronically programmable valves capable of being configured to alter fluid steering in the fluid tracks;
  c) a means for the array to interface with the fluid tracks;
  d) a means to control fluid flow in the fluid tracks; and
  e) user interface to direct control of valves via control logic within the device;
  wherein, by the interface, valves positions are controllable and alterable and by this alteration and reconfiguration, fluid tracks may be manipulated.

Preferred aspects and advantages of the invention:
Valve and microreactor configurations can be determined/ generated by past/present/future microreactor states Runtime user valve "smart" interactions are allowed during sample processing (wherein user interface, delivering content from the device, cues and prompts user to alter configuration (whether in a new way or pre-programmed way)

Heterogenous samples are processed (not just mixed samples and heterogenous rectors but individualized/customized processing of individual samples)

Interconnect can be reused via "blanking" stages but wherein dirty sections can be tagged so that they can be excluded from use in subsequent sample mappings, allowing the full remainder of the interconnect to be used for subsequent processing The provision of "clocking" of sample movement to create sequential processing and finite state machines Multi-channel interconnect in one aspect, in a single plane These fluid tracks are configurable via valve systems which are preferably either hydrogel or magnetically actuated. If the former, the valve is capable of being configured to alter fluid steering in the fluid tracks preferably by the application of heat. If the latter, the valve is capable of being configured to alter fluid steering in the fluid tracks by the application of a magnetic force.

It is preferred that the device of the present invention additionally comprises one or more sensors to aid in fluid analysis. There are a variety of possible sensor arrangements but in a preferred form, the sensor is one of an electro-impedance sensor, pH sensor, or an optical sensor. So, in operation, the device of the present invention comprises an electronic control board and a display for sensor readings. These sensors may include thermal sensors for polymerase chain reaction thermal control, or electrochemical or optical sensors for monitoring chemical reaction reporters.

It is preferred that the cartridge is disposable and that substantially entirely the remainder of the device is reusable. It is preferred that the cartridge includes a sample solution access point/ingress means. It is preferred that the means for the valve array to interface with the fluid tracks is a flexible membrane. Mostly preferably, this membrane is made of poly dimethylsilozane (PDMS) or other thermosetting or thermoplastic elastomer.

It is preferred that the device of the present invention is portable. The device may be tagged to indicate its general interconnect topology. Such tagging may be accomplished by use of tags selected from the group consisting of an RF id tab, bar encoding, and other read only or read-writable tags.

Valves

The microvalve is one of the most important microfluidic components as it precisely regulates flow in microfluidic systems. The control of liquid flow is generally accomplished by a microvalve actuator that performs mechanical work and deflects in response to external stimuli. A deformable diaphragm is the basic structure of many such microvalves (although the present invention is not limited to such diaphragms) and its main function is to provide a mechanism for the desired actuation method to produce useful displacements and force the microvalve to open or close.

Within the scope of the present invention, it is desirable that the device comprises at least one programmable valve and such valve preferably may be opened or closed using digital values of '0' and '1', effectively acting as switches to open/close the connection between two fluidic tracks. In one aspect, the valve(s) may be digitally opened and closed to direct fluid to flow onto and off of the device as well as between wells/channels. Digital control, in one aspect, refers to control by a computer system.

Many different microvalves have been successfully demonstrated that utilize a plurality of actuation schemes, including, but not limited to magnetic, electrostatic, mechanical, material phase-change, and piezoelectric actuation schemes (to name a few). Some of these valves are based in traditional microelectromechanical systems (MEMS) materials such as silicon and may be used within the scope of the present invention.

The key technology related to the reconfigurable microfluidic array of the present invention is one or more dynamically programmable valves. Such fluid steering, via valve manipulation, can be accomplished most preferably by the use of either:

1) phase-change hydrogel based valves, including, but not limited to plug type and diaphragm actuators; and 2) magnetic polymer nanocomposite valves.

Most preferably, these are thermally-responsive hydrogel actuators/hydrogel microvalves that can be actuated via digital logic levels and magnetic polymer actuators that can be deflected sufficiently for valve operation, and actuated via digital logic levels.

Preferred Hydrogel Valves

Hydrogels are excellent materials for polymer-based microvalve actuation due to their biocompatibility and energy conversion efficiency, and their ability to deflect polymer membranes which can be employed as microvalve actuators. Hydrogels have been investigated extensively for biomedical and microfluidic applications due to their ease of actuation, and large degrees of swelling and de-swelling that can be realized through changes in temperature or pH.

Hydrogel-based valves have many advantages such as simple fabrication and operation, good sealing, and tolerance for high pressure. Fluid polymers that may be employed for microfluidics of hydrogel actuators include all generally accepted microfluidics materials and also: elastomers (e.g., polydimethylsiloxane (PDMS)), and other thermosetting and thermoplastic elastomers for the valve diaphragm, silicon, glass, ceramic, polycarbonate, SU-8 and other epoxies, polymethylmethacrylate, polyurethane, and polyethylene and the like. Example suitable hydrogels include: poly(N-isopropylacrylamide (PNIPAAm).

Figure 3:
FIG. 3 is a photomicrograph of a thermally-responsive hydrogel-driven polymer diaphragm suitable for use in microvalve array; the PDMS diaphragm my be operated by PNIPAAm hydrogel using microheaters.

FIG. 3 is a photomicrograph of a thermally-responsive hydrogel-driven polymer diaphragm suitable for use in microvalve array. The PDMS diaphragm is operated by PNIPAAm hydrogel using microheaters.

Preferred Magnetic Valves:

In another embodiment, a flow control device (the valve) is magnetically actuated. Generally, magnetic actuation requires a field generator and a magnetic (i.e. paramagnetic or ferromagnetic) element. The magnetic element moves in response to application of a magnetic field, with the direction of motion of the magnetic element depending on the direction of the applied magnetic field. Opening or closing force of a magnetically actuated valve may be adjusted by varying the magnitude of the applied magnetic field, or selecting a magnetic element with appropriate response characteristics (e.g., magnetization). For example, if strong magnetization and/or bi-directionality of motion is desirable, then magnetic elements formed from rare earth magnetic materials may be used.

Preferably, at least one magnetic element is integrated into a microfluidic flow control device and used in conjunction with a deformable membrane or other actuator element (e.g., cantilever structure). In a preferred embodiment, a deformable membrane includes one or more discrete magnetic elements.

As an alternative to using one or more discrete magnetic elements, a flexible membrane comprising a diffuse magnetic layer may be provided. If a diffuse magnetic layer is used, then it is preferably coupled to a deformable membrane selected for desirable material properties such as chemical compatibility or sealing characteristics. The magnetic field generator preferably comprises a coil of current-carrying wire, preferably insulated wire. Current may selectively applied to the coil, such as by using an external current source, to generate a magnetic field. The strength of the magnetic field may be adjusted by varying the magnitude of the current and the number of turns of wire. The direction of the resulting magnetic field is parallel to the central axis of the coil. In a more preferred embodiment, a field-concentrating element, such as a ferromagnetic core, is provided along the central axis of the coil. The field-concentrating element is preferably substantially cylindrical in shape, and if a highly focused field is desired then the cylinder should be of a small diameter. The current-carrying wire may be directly wrapped around the field-concentrating element.

Preferably include hard magnetic particles and nanoparticles which include: FeC, CoFe, CoFeZn, $Ni_{0.5}Co_{0.5}Fe_2O_4$, $Zn_{0.5}Co_{0.5}Fe_2O_4$, $Zn_{0.5}Ni_{0.5}F$, NdFeB, $CoFe_2O_4$, $NiFe_2O_4$, $ZnFe_2O_4$, $Ni_{0.5}Co_{0.5}Fe_2O_4$, $Zn_{0.5}Co_{0.5}Fe_2O_4$, $Zn_{0.5}Ni_{0.5}Fe$, $SrFe_{12}O_{19}$, MQFP $((Nd_{0.7}Ce_{0.3})_{10.5}Fe_{83.9}B_{5.6})$ or combinations thereof. Further details are provided in US 20110151377, which is incorporated herein by reference. Magnetic valves also include all suitable nickel-based, iron-based materials, or any other soft magnetic materials. These materials may be either used directly as films or cut magnets placed in a polymer membrane, or employed as micro/nano powders in a micromoldable polymer base to form the flexible nanocomposite materials to make the membrane.

In achieving functionality, these valves may rely solely on electronic signals sent to either micromagnetic coils or heater elements. FIGS. 2a and 2b show an example of magnetic elastomers developed in accordance with the present invention and most preferably wherein magnetic-nanoparticles are embedded in polydimethylsiloxane (PDMS) and wherein the nanocomposite was poured over a PMMA actuator micromold (further details provided below in the examples). By way of illustration and not limitation, within these valves, both magnet and membrane were doped uniformly w/75 wt % 5 µm $(Nd_{0.7}Ce_{0.3})_{10.5}Fe_{83.9}B_{5.6}$/PDMS. The thickness of membranes, magnets: 100, 500 µm, the size of membranes ranged 1 to 8 mm on a side, and central magnets 0.4 to 3.6 mm on a side. Within FIG. 2a, actuator membrane is 22, PMMA Enclosure Top Piece is 24 and PMMA Enclosure Top Piece is 26. Within FIG. 2b, central magnet is 28, membrane is 30 and alignment mark is 32.

As used herein, the term "micro-coil" refers to a miniature commercial electromagnet and/or microscale electromagnet via electroplating or PCB or plexiglass mirror patterning.

In FIG. 1, there is provided generally at 10 a microfluidics multiplexing device for biological and chemical sample analysis. Components are as noted:

Sensor Read-Out (12):

The sensor readout module translates signals between the on-board sensors and the digital interface to the compute platform (for example, an FPGA-based System-on-[Programmable]-Chip) for reading and interpreting sensor values. This translation may involve amplification or other electronic signal conditioning. It is preferred that it is re-usable even if the sensors that are used are not (although it is also preferred that the sensors are re-usable as well).

Sensor Module (for Example qPCR) is at 13

The sample chambers are preferably open on one side to allow a sensor module to be snapped into place to make contact with sample solution, and interfaced to the sensor read-out board and control board electronics via microelectronic contacts. The sensor module technology is based on microfluidic and electronic mechanical attachment structures (e.g., peg-in-hole interfaces similar to IC-in-socket attachment), and contain sensors and other devices (e.g., heaters for qPCR if the user-defined program involves qPCR). While fluorescence detection is conventionally employed for sensors in many biological processes such as qPCR, impedance and/or pH label-free detection for qPCR could also be employed for the example qPCR. It is noted that qPCR is used by example only; for other tasks, other sensors or support structures may be needed for the "sensor module".

Microfluidic World to Chip Modules is at 15

Microfluidic World-to-Chip Modules:

The ports shown are for example only. The world-to-chip modules consist of any sort of ports, wells, or other structures for getting sample fluid on and off chip.

Microfluidic Track and Chamber Module (14):

The microfluidic tracks and chambers are the physical structures through which fluid is manipulated by the instrument in a controlled manner. The chambers are where biochemical or other processes may proceed and/or be detected depending on the user-programmed task (e.g., where qPCR thermal cycling and detection may occur if the user-programmed task involves qPCR). Each chamber may have access to one or more fluidic tracks, where a collection of fluidic tracks with the same directionality form a "channel." Although the network of fluidic tracks is expected to be two dimensional, the intersection points between tracks of different directionality may be multi-dimensional to increase the potential routability of samples for processing (not shown here to simplify the illustration).

Micromagnetic Valve Stopper Module (16):

This is shown for the embodiment wherein magnetic valve actuators may be used. In this instance, the stoppers are flaps, cantilevers, diaphragms, or other physical structures will prevent fluid flow in a valve-like manner, which are either consisting of or actuated by small magnets. If, for example, thermally actuated hydrogel valves are used instead, this would consist of either plugs of hydrogel for actuating membranes or directly stopping fluid under gelling. For other valve types, these would consist of other valve opening and closing actuators or structures. A corresponding "latching" mechanism may also be used to hold the valves in place and close off/open up the flow of fluid through a fluidic track to reduce run-time power consumption and/or improve durability. These latches would typically be on the opposite side of the microfluidic track and chamber module (not shown here to simplify the illustration) and may require an additional interface layer with the electronic control board to control the latches at run time.

Micro Electromagnet Module (18):

This module may contain microelectromagnets (for the case of magnetic valves), heaters (for the case of thermally-responsive hydrogel valves or other thermally actuated valves, such as shape memory alloy) or other structures that are electronic in nature with each one directly controlling valve actuators. This may also involve amplification or other electronic signal conditioning.

Electronic Control Board (20):

The electronic control board will include the system's compute platform used to evaluate how samples should be mapped and routed onto a given cartridge (preferably comprising all the layers from the sensor module to the micromagnetic valve stopper module) for processing. It will interface with the sensor read-out module to allow run-time processing and routing decisions based on the sensor values. It will also interface with the micro-electromagnet module to configure the routing tracks to load, process and unload samples at "run-time." It may also interface with the microfluidic track and chamber module if needed to control additional latching mechanisms for the valves. Along with the numerous outputs used to control the valves, and latches if needed, and the numerous inputs to read the sensors, the compute platform may include amplication/de-amplification or other electronic signaling conditioning including, but not limited to multi-plexing and de-multiplexing of the inputs and outputs.

The compute system preferably also comprises a user-interface as well as a processing unit and a storage/memory unit capable of evaluating algorithms based on the user-entered constraints and processing requests entered for the samples and the specific sensor configuration on the specific cartridge loaded into the device at run time.

FIG. 3 shows a gelling thermally responsive hydrogel 34 as heat is applied. Valve actuation using thermally responsive hygrogels can be made easily using only electronic control signals.

FIGS. 4a-4d show flexible tungsten heaters employed to gel a thermally responsive hydrogel. Stimuli-responsive hydrogels are currently the focus of intense research in microfluidic sample steering and cell culture.

Figure 6:
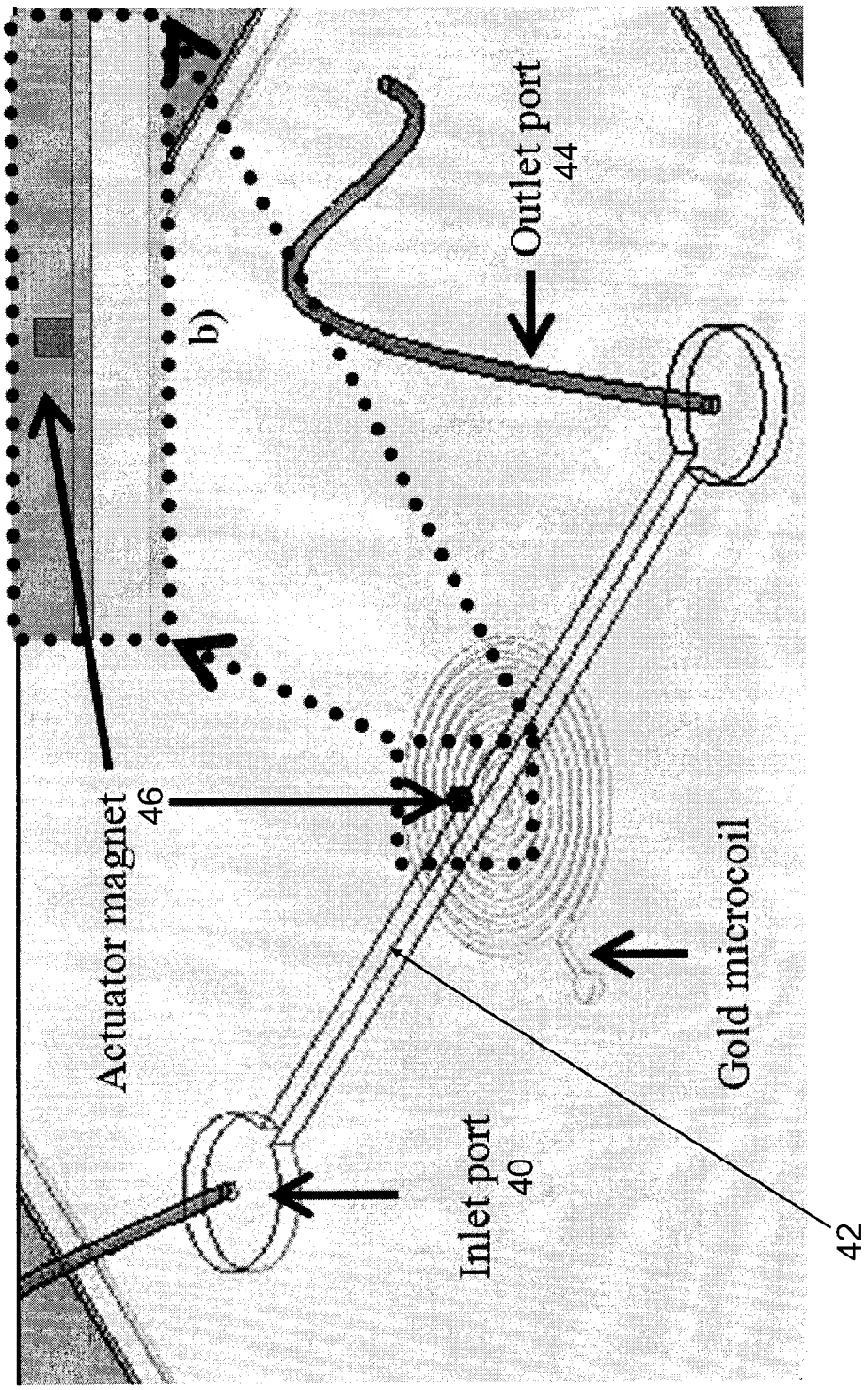
FIG. 6 illustrates fluid flow manipulation in the device by magnetic valves.

FIG. 6 illustrates basic fluid flow manipulation in the device of the present invention, as manipulated by a magnetic valve. Fluid enters an inlet port, travels along a track or microchannel 42 and exits (as elutant) via an outlet port 44. Micromagnet 46 can be pulled or pushed by on-chip electromagnetic (for example, a gold microcoil) or miniature electromagnet. Pulling micromagnet down seals the track or microchannel, stopping fluid flow. If coil located above, the micromagnet can "push" instead, or in addition to pull.

Figure 7:
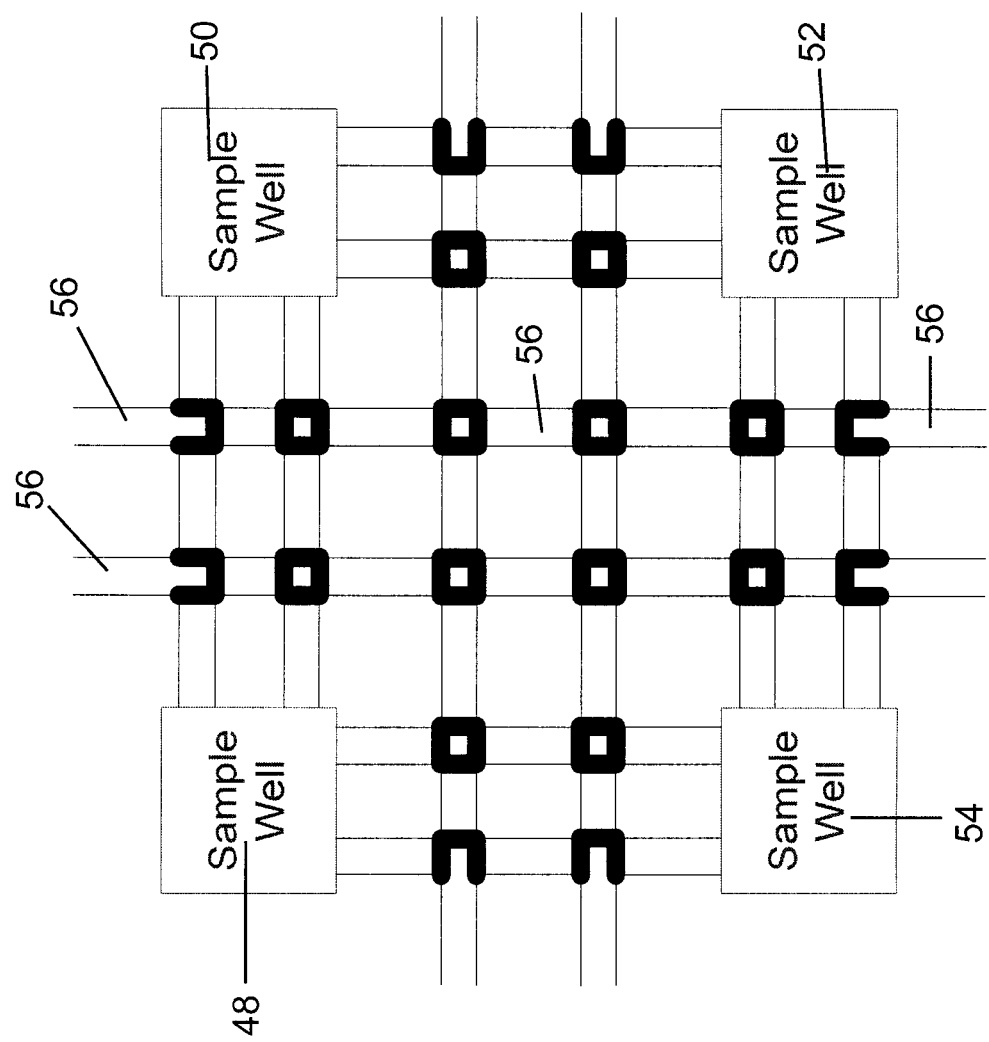
FIG. 7 is an illustration of showing one configuration of a fluid track routing between sample wells.

FIG. 7, this is an example only showing one configuration of a fluid track routing between sample wells 48, 50, 52 and 54 along tracks 56. The "sample well" is simply a well that holds a sample and in which an analysis operation may be performed. The valves show potential valve placement for routing between wells in a reconfigurable manner.

The device of the present invention comprises a compute platform that is capable of interfacing with numerous inputs (e.g. sensor outputs) and numerous outputs (used to control the valves that open and close the fluidic tracks). The platform must also be able to interpret user-defined sample constraints and apply appropriate algorithms to assign sample(s) to the appropriate sensor(s) for processing and ensure that samples are routed on the fluidic tracks to minimize resource usage, while guaranteeing that there is no sample contamination. The ability to apply these algorithms and interpret user-constraints at runtime requires a programmable processing unit (such as a processor) as well as a memory unit to store the algorithms used to assign and route the samples for processing and support a run-time user-interface.

In today's technology, these constraints can be met with a System-on-chip architecture combined with additional off-chip memory for program storage. Due to the number of I/Os involved, as well as the programming complexity and desire for parallel control, the currently preferred technology is a Field Programmable Gate Array, which provides numerous I/Os that can be independently configured in parallel at run-time configurable as well as sufficient compute resources to support the instantiation/inclusion of a processor on the same die to perform the necessary algorithmic computations as well.

While for larger volumes of scale, a standard cell or custom ASIC with more limited configurability may be appropriate, any computing platforms that meets the defined requirements to: 1) support the user interface, 2) perform the necessary computations, and 3) read in the sensor values/control the valves would also be acceptable.

Microfluidic devices providing flow control utility according to the present invention may be fabricated in various ways using a wide variety of materials. In an especially preferred embodiment, microfluidic devices according to the present invention are constructed using stencil layers to define channels and/or chambers. A stencil layer is preferably substantially planar and has microstructure cut through the layer. For example, a computer-controlled plotter modified to accept a cutting blade may be used to cut various patterns through a material layer. Alternatively, a computer-controlled laser cutter may be used. As further alternatives, conventional stamping, cutting, and/or molding technologies may be employed to form stencil layers. The wide variety of materials that may be used to fabricate microfluidic devices using sandwiched stencil layers include polymeric, metallic, and/or composite materials, to name a few. Notably, use of stencil-based fabrication methods enables a particular device design to be rapidly "tuned" or optimized for particular operating parameters, since different material types and thicknesses may be readily used and/or substituted for individual layers within a device. The ability to prototype devices quickly with stencil fabrication methods permits many different variants of a particular design to be tested and evaluated concurrently.

When assembled in a microfluidic device, the top and bottom surfaces of stencil layers may mate with one or more adjacent stencil or substrate layers to form a substantially enclosed device, typically having one or more inlet ports and one or more outlet ports.

The microfluidic device of the present invention comprises a plurality of tracks, wherein each track has an inlet and at least one outlet. In some embodiments, the microfluidic device comprises at least about 10, or at about least 20, or at about least 30, or at about least 40, or at about least 50, or at about least 60, or at about least 70, or at about least 80, or at about least 90, or at about least 100, or at about least 120, or at about least 140, or at about least 150, or at about least 160, or at about least 180, or at about least 200, or at about least 220, or at about least 240, or at about least 260, or at about least 280, or at about least 300, or at about least 320, or at about least 340, or at about least 360, or at about least 380, or at about least 400 tracks, or more than 400 tracks or any integer between 10 and 400 tracks. In some embodiments, the microfluidic device comprises at least about 32, or at least 48 or at least about 96, at least about 384 tracks, or at least about 768 tracks, or at least about 1536 tracks or greater than 1536 tracks.

In some embodiments, the tracks are compatible with automated pipettors for sample transfer (i.e. sample transfer to inlet sample wells or sample transfer from outlet sample wells (i.e. negative and positive sample wells)) of the microfluidic device. In some embodiments, the tracks are configured using a three-dimensional micromachining method, such as a mechanically machined base/laminated cyclic polyolefin window.

Microfludic chips can be configured by one of ordinary skill in the art to be any geometric shape and size, and are generally small and flat, typically about 1 to 10 inches square (25 to 250 mm square) or rectangles with dimensions of about 25 to 200 mm. The volume of sample flowing through the microfluidic chip will be small. For example, they will contain only about 0.1 to 10 .mu.l for each assay, although the total volume of a specimen may range from 10 to 200 .mu.l. The chambers holding the sample fluids and reagents typically will be relatively wide and shallow in order that the samples can be easily seen and changes resulting from reaction of the samples can be measured by suitable equipment. The interconnecting capillary passageways typically will have a cross-sectional dimension in the range of 1 to 2000 μM preferably 200 to 500 μM. The shape will be determined by the method used to form the passageways but passageways having rectangular cross-sections are preferred. The depth of the passageways will be at least 5 μM in many practical applications where samples contain particles, but may be smaller where the nature of the sample permits.

While there are several ways in which the tracks can be formed, such as thermoset micromolding, injection molding, laser ablation, diamond milling or embossing, it is preferred to use injection molding in order to reduce the cost of the chips. Generally, a base portion of the chip will contain the desired network of tracks. After reagent compounds have been placed in the chambers as desired, a top portion will be attached over the base to complete the chip.

In some embodiments, the chips can be disposable, and are intended to be disposable after a single use. Consequently, they will be made of inexpensive materials to the extent possible, while being compatible with the reagents and the samples which are to be analyzed. In many instances, the chips will be made of plastics such as polycarbonate, polystyrene, polyacrylates, or polyurethene, poly methyl methacrylate, alternatively, they can be made from silicones, silicates, glass, wax or metal.

Referring specifically now to FIG. 1, there is provided a μROAMS platform and a model of the reconfigurable microfluidic track network. Samples are directed within the device, similar to electrons in an integrated circuit, to be stored, tested, and moved off-device as desired. The control of the valves is programmed on-site to perform the needed functions via a simple user interface and a synthesis flow to convert a user's description into a "configuration bit-stream" to control the valves.

Preferably, (1) development of the circuitry connecting the coils and FPGA; (2) the FPGA user interface; and (3) demonstration of control of both single and arrayed valves the interface will be implemented as software running on a Microblaze processor on the FPGA.

The reconfigurable technology within the device of the present invention, in contrast to currently used devices, features new electronically programmable microvalves controlled in a most preferred form via either electromagnets or heaters. These are analogous to configuration switches in Field Programmable Gate Arrays (FPGAs). These valves are employed to perform fluid steering in fluid tracks (tracks). It is to be understood that other valve manipulation means are fully within the scope of the invention. Although the fluidic track network may be planar in nature, to increase the connectivity between the 2D fluidic track channels, multi-dimensional (i.e. 3D "switch block" connectivity patterns) may be used to increase the potential routability of samples.

In a preferred form, the present invention adapts silicon-based field-programmable gate array (FPGA) architectural and synthesis concepts to the world of microfluidics. Conceptually, one preferred reconfigurable microfluidics array resembles an FPGA (see FIG. 1). Previous work to reduce FPGA area by limiting the number of switches are adapted to this microfluidics platform to reduce the number of valves used to provide connectivity between fluidic tracks used to route samples. As modern FPGAs allow complete Systems-on-Chip (SoCs) and have a large number of Inputs and Outputs (I/Os), an FPGA will be used to implement the user interface and control the valve-positions via "configuration bits" mapped to the FPGA's I/Os. Depending on the inputs provided to the user interface, the control logic implemented on the FPGA will reconfigure the valve positions to match these new specifications. This functionality has been adapted herein for a microfluidics platform.

FIG. 1 shows a conceptual diagram of μROAMS. The sample chambers are open on one side to allow a sensors module to be snapped into place to make contact with sample solution, and interfaced to board electronics via microelectronic contacts. The sensor module technology will be based on microfluidic and electronic attachment structures previously devised by authors herein, and contain sensors and other devices (such as heaters for qPCR).

Limiting the Number of Reconfigurable Valves:

an important architectural investigation is the number of valves and fluidic tracks available to "route" samples to the array's sensors to reduce area. This is akin to the challenge faced by FPGA researchers: even if there is sufficient logic on a chip for a design, the fixed number of tracks in the interconnect may be insufficient to route designs that use most of the chip's logic. Reducing the number valves or fluidic tracks reduces the number of paths a sample may take. To process multiple samples in parallel, algorithms that are able to find a unique path for each sample given the constraints of the sample(s) being processed/evaluated and the fixed resources inherent to the specific instantiation of a cartridge architecture are preferably used.

Sample-to-Sample Contamination and Cross-Talk for Tests Employing Multiple Samples:

Contamination can be a huge problem in any laboratory testing environment/instrumentation. Within the operation of the device of the present invention, a system is provided to flush the system (i.e. a "blanking" stage) between samples loading at an "input" port, and to treat the surfaces of the device to prevent analyte attachment. Also, as described herein, the fluid "routing" algorithms will ensure "good" results remain uncontaminated.

It is to be understood, with respect to operation of the device, that the analysis steps may be different depending on the particular testing to be completed and the sample to be analyzed and such differences are fully within the purview of a skilled technician in this field to understand. For example, the steps to perform qPCR on water samples versus blood, or to perform qPCR versus microassembly of blocks fluidically steered between chambers or antibody monitoring for cell toxicity studies, are completely different. The constant and a key aspect of the invention as provided herein is the provision of dynamically reconfigurable fluid arrays.

Operation:

In operation, the device of the present invention may be operated by a user in a preferred manner as described herein:

Following the preparation of one or more samples, a user loads a cartridge that includes one or more desired sensor(s) into the device housing. Cartridges may have different configurations with different numbers and types of sensors. Upon loading the cartridge, an electronic control board will "read" the cartridge label describing its sensor configuration and use that to evaluate the validity and legality of all user requests for samples on the device. "New" cartridge configurations can be added to the device as "patches" (e.g. in the form of libraries) to the device software after it has been distributed to the user. This will allow the device to adapt and support additional cartridge configurations over time.

1) Via the user interface that communicates with the compute platform on the electronic control board, the user would enter a series of constraints that describes the number of samples being processed and the desired processing via the sensor(s) and any interdependencies between sample(s) and the sensor(s) output(s).

2) Before the device requests that the user loads the samples into the device cartridge, the compute platform (in our example realized by a System-on-Chip implemented on a FPGA) would parse the user entered constraints and:

a. First verify that they are logically correct—if not the user will be asked for additional information/presented with an error message b. Second verify that the processing requested of the device matches the capabilities supported by the current cartridge (e.g. of none of the sensors in the given cartridge support qPCR, then this request would be considered invalid).

c. Determine a valid assignment of sample(s) to the existing sensor(s) as well as their corresponding fluidic track connectivity patterns necessary to route the sample(s) to the sensor(s) to minimize resource usage (e.g. fluidic tracks and sensors) while guaranteeing that no samples are contaminated.

d. Once the fluidic track connectivity patterns had been determined, the compute platform would configure the micro-electomagnet module via the I/Os on the electronic control board and any additional mechanisms needed to manipulate the valves (e.g. a latching mechanism).

3) The user would then load the sample(s) as directed by the user interface into the device cartridge via the microfluidic world-to-chip module interface.

4) The fluidic samples would then travel from the microfluidic world-to-chip modules via the microfluidic tracks to the chamber modules for evaluation via their corresponding sensors in the sensor module.

5) Once sufficient time has elapsed, the sensor(s)' output would be read via the sensor read-out module to the electronic control board to the compute platform for evaluation.

6) Based on the evaluation of the sensor data with respect to the constraints provided by the user initially, or after an additional prompt from the user for further processing with additional constraints, the sample fluid(s) may be need to be routed to an additional set of sensors for additional processing or determined as waste that can be off-loaded from the device via the world-to-chip modules. The constraints that will be used by the compute platform to determine if this additional processing is possible on the current cartridge will be evaluated as outlined in step 3. Step 4 would then be repeated and the fluidic samples that are to undergo a second round of processing would either travel from their current chamber module where they were previously "evaluated" via a sensor to a new chamber module and corresponding sensor or the user would be prompted to load additional fluid from that sample for further processing via the microfluidic world-to-chip modules.

7) Steps 6 and 7 may be repeatedly performed depending on the number of samples and sensors available on the cartridge.

8) Once the user has completed processing with that cartridge, it may be removed and replaced with a new (similar) cartridge or a cartridge with a different configuration.

9) Steps 1-8 can be repeated anytime a user wishes to operate the device and evaluate sample(s).

Computing System

Unless specifically stated otherwise, it is appreciated that throughout the description, discussions utilizing terms such as "processing" or "computing" or "calculating" or "determining" or "displaying" or the like, refer to the action and processes of a data processing system, or similar electronic computing device, that manipulates and transforms data represented as physical (electronic) quantities within the computer system's registers and memories into other data similarly represented as physical quantities within the computer system memories or registers or other such information storage, transmission or display devices.

The algorithms and displays with the applications described herein are not inherently related to any particular computer or other apparatus. Various general-purpose systems may be used with programs in accordance with the teachings herein, or it may prove convenient to construct more specialized apparatus to perform the required machine-implemented method operations. The required structure for a variety of these systems will appear from the description below. In addition, embodiments of the present invention are not described with reference to any particular programming language. It will be appreciated that a variety of programming languages may be used to implement the teachings of embodiments of the invention as described herein.

An embodiment of the invention may be implemented as a method or as a machine readable non-transitory storage medium that stores executable instructions that, when executed by a data processing system, causes the system to perform a method. An apparatus, such as a data processing system, can also be an embodiment of the invention. Other features of the present invention will be apparent from the accompanying drawings and from the detailed description which follows.

The systems and methods described herein rely on a variety of computer systems, networks and/or digital devices for operation. As will be appreciated by those skilled in the art, computing systems and web-based cross-platforms include non-transitory computer-readable storage media for tangibly storing computer readable instructions. In order to fully appreciate how this preferably web-based cross-platform application and system operates an understanding of suitable computing systems is useful and is provided herein.

As used herein, "stored" refers to a process for encoding information on the storage device. Those skilled in the art can readily adopt any of the presently known methods for recording information on known media to generate manufactures comprising the sequence information or expression level information.

In some embodiments of this aspect and all other aspects of the present invention, data is acquired from the microfluidics device and stored in the storage device, such data being obtained from detectors of the sample passing through the tracks of the microfluidic device. In some embodiments, the data is reference image data, from stored line-scan images of references (for example, cells or reference cell phenotypes). Alternatively, the data is reference data from a database. In one embodiment the data is reference data or models that are indicative of a specific cell, cell phenotype, cell features, protein localization etc. . . . .

In one aspect, a computer system (or digital device), which may be understood as a logic apparatus adapted and configured to read instructions from media and/or network port, is connectable to a server and can have a fixed media. The computer system can also be connected to the Internet or an intranet. The system includes central processing unit (CPU), disk drives, optional input devices, such as a key-board and/or mouse and optional monitor. Data communication can be achieved through, for example, communication medium to a server at a local or a remote location. The communication medium can include any suitable means of transmitting and/or receiving data. For example, the communication medium can be a network connection, a wireless connection or an Internet connection.

It is envisioned that data relating to the present disclosure can be transmitted over such networks or connections. The computer system can be adapted to communicate with a participant and/or a device used by a participant. The computer system is adaptable to communicate with other computers over the Internet, or with computers via a server. Each computing device (including mobile devices) includes an operating system (OS), which is software, that consists of software programs and data that runs on the devices, manages the device hardware resources, and provides common services for execution of various application software. The operating system enables an application program to run on the device.

As will be appreciated by those skilled in the art, a computer readable medium stores computer data, which data can include computer program code that is executable by a computer, in machine readable form. By way of example, and not limitation, a computer readable medium may comprise computer readable storage media, for tangible or fixed storage of data, or communication media for transient interpretation of code-containing signals. Computer readable storage media, as used herein, refers to physical or tangible storage (as opposed to signals) and includes without limitation volatile and non-volatile, removable and non-removable storage media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

A user launches an app created by an app creator and downloaded to the user's mobile device to view digital content items and can connect to a front end server via a network, which is typically the Internet, but can also be any network, including but not limited to any combination of a LAN, a MAN, a WAN, a mobile, wired or wireless network, a private network, or a virtual private network. As will be understood a very large numbers (e.g., millions) of users are supported and can be in communication with the website via an app at any time. The user may include a variety of different computing devices.

Application delivery platform can be implemented entirely in hardware and/or a combination of hardware and/or software in execution. Further, application delivery platform can be incorporated within and/or associated with other compatible components. Additionally, application delivery platform can be, but is not limited to, any type of machine that includes a processor and/or is capable of effective communication with network topology and/or cloud. Illustrative machines that can comprise application delivery platform can include desktop computers, server class computing devices, laptop computers, notebook computers, Tablet PCs, consumer and/or industrial devices and/or appliances, hand-held devices, and the like.

Network topology and/or cloud can include any viable communication and/or broadcast technology, for example, wired and/or wireless modalities and/or technologies can be utilized to effectuate the claimed subject matter. Moreover, network topology and/or cloud 104 can include utilization of Personal Area Networks (PANs), Local Area Networks (LANs), Campus Area Networks (CANs), Metropolitan Area Networks (MANs), extranets, intranets, the Internet, Wide Area Networks (WANs)—both centralized and/or distributed—and/or any combination, permutation, and/or aggregation thereof. Furthermore, as those skilled in the art will appreciate and understand various data communications protocols (e.g., TCP/IP, Ethernet, Asynchronous Transfer Mode (ATM), Fiber Distributed Data Interface (FDDI), Fibre Channel, Fast Ethernet, Gigabit Ethernet, Wi-Fi, Token Ring, Frame Relay, etc.) can be utilized to implement suitable data communications.

Additionally application delivery server/platform may include a provisioning component that, based at least in part on input received from a portal component, can automatically configure and/or provision the various disparate mobile devices with appropriate applications.

In some embodiments, the data acquired by the microfluidics device can be read by a storage device. As used herein the "storage device" is intended to include any suitable computing or processing apparatus or other device configured or adapted for storing data or information. Examples of electronic apparatus suitable for use with the present invention include stand-alone computing apparatus; communications networks, including local area networks (LAN), wide area networks (WAN), Internet, Intranet, and Extranet; and local and distributed processing systems. Storage devices also include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon sequence information or expression level information. The data are typically provided in digital form that can be transmitted and read electronically, e.g., via the Internet, on diskette, or any other mode of electronic or non-electronic communication.

So, it is to be fully appreciated that a storage device can comprise, for example, volatile memory or non-volatile memory, or can include both volatile and non-volatile memory. By way of illustration, and not limitation, non-volatile memory can include read-only memory (ROM), programmable read only memory (PROM), electrically programmable read only memory (EPROM), electrically erasable programmable read only memory (EEPROM), or flash memory. Volatile memory can include random access memory (RAM), which can act as external cache memory. By way of illustration rather than limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink® DRAM (SLDRAM), Rambus® direct RAM (RDRAM), direct Rambus® dynamic RAM (DRDRAM) and Rambus® dynamic RAM (RDRAM). Storage device of the subject invention is intended to comprise, without being limited to, these and any other suitable types of memory. In addition, it is to be appreciated that the storage device can be a server, a database, a hard drive, and the like.

Server Modules, Components, and Logic

Certain embodiments are described herein as including logic or a number of modules, components or mechanisms. A module, logic, component or mechanism (hereinafter collectively referred to as a "module") may be a tangible unit capable of performing certain operations and is configured or arranged in a certain manner. In example embodiments, one or more computer systems (e.g. server computer system) or one or more components of a computer system (e.g., a processor or a group of processors) may be configured by software (e.g., an application or application portion) as a "module" that operates to perform certain operations as described herein.

In various embodiments, a "module" may be implemented mechanically or electronically. For example, a module may comprise dedicated circuitry or logic that is permanently configured (e.g., within a special-purpose processor) to perform certain operations. A module may also comprise programmable logic or circuitry (e.g., as encompassed within a general-purpose processor or other programmable processor) that is temporarily configured by software to perform certain operations.

Accordingly, the term "module" should be understood to encompass a tangible entity, be that an entity that is physically constructed, permanently configured (e.g., hardwired) or temporarily configured (e.g., programmed) to operate in a certain manner and/or to perform certain operations described herein. Considering embodiments in which modules or components are temporarily configured (e.g., programmed), each of the modules or components need not be configured or instantiated at any one instance in time. For example, where the modules or components comprise a general-purpose processor configured using software, the general-purpose processor may be configured as respective different modules at different times. Software may accordingly configure the processor to constitute a particular module at one instance of time and to constitute a different module at a different instance of time.

Modules can provide information to, and receive information from, other modules. Accordingly, the described modules may be regarded as being communicatively coupled. Where multiple of such modules exist contemporaneously, communications may be achieved through signal transmission (e.g., over appropriate circuits and buses) that connect the modules. In embodiments in which multiple modules are configured or instantiated at different times, communications between such modules may be achieved, for example, through the storage and retrieval of information in memory structures to which the multiple modules have access. For example, one module may perform an operation, and store the output of that operation in a memory device to which it is communicatively coupled. A further module may then, at a later time, access the memory device to retrieve and process the stored output. Modules may also initiate communications with input or output devices, and can operate on a resource (e.g., a collection of information).

While the forms of node/apparatus, method and system described herein constitute preferred embodiments of this invention, it is to be understood that the invention is not limited to these precise forms. As will be apparent to those skilled in the art, the various embodiments described above can be combined to provide further embodiments. Aspects of the present systems, methods and nodes (including specific components thereof) can be modified, if necessary, to best employ the systems, methods, nodes and components and concepts of the invention. These aspects are considered fully within the scope of the invention as claimed. For example, the various methods described above may omit some acts, include other acts, and/or execute acts in a different order than set out in the illustrated embodiments.

Further, in the methods taught herein, the various acts may be performed in a different order than that illustrated and described. Additionally, the methods can omit some acts, and/or employ additional acts.

These and other changes can be made to the present systems, methods and articles in light of the above description. In general, in the following claims, the terms used should not be construed to limit the invention to the specific embodiments disclosed in the specification and the claims, but should be construed to include all possible embodiments along with the full scope of equivalents to which such claims are entitled. Accordingly, the invention is not limited by the disclosure, but instead its scope is to be determined entirely by the following claims.

Example 1 Valve Creation—Micropatterning the Poly(N-Isopropyacrylamide) Hydrogel In order to make hydrogel microstructures in one way, the bulk hydrogel was first spin-coated onto a glass/Pyrex™ wafer. We then compressed the thin film hydrogel layer between two glass plates and a PMMA mold with the negative of the desired features, and then put the assembly into a vacuum chamber for 30 minutes. This significantly improves the precision of the hydrogel insertion into the track and response time compared to our previous result where we employed hydrogel-actuated membranes and manually cut hydrogel actuation elements. The final patterned hydrogel structure is a 500 μm wide square and with depth of 1000 μm.

Example 2 Valve Creation—PNIPAAm Hydrogel Synthesis

NIsopropylacrylamide (NIPAAM) was used as the major monomer for hydrogel synthesis. NIPAM forms a three dimensional hydrogel when crosslinked with N,N'-methylenebisacrylamide (MBAAm)20. Ammoniumpersulfate (APS initiator), N,N' methylenebisacrylamide (BIS, crosslinker), N'N,N'N'tetramethylethylenediamine (TEMED, accelerator), acrylamide (AAm, reservoir layer) were all obtained from Sigma Aldrich corporation. The polyNIPAAm gel was made by free radical polymerization of monomer NIPAAm. The crosslinking agent MBAAm and monomer NIPAM were first dissolved in de-ionized water (DI H2O) for 12 hours with a constant supply of N2 source (oxygen free environment). The initiator APS, and the accelerator, TEMED, were then added to the solution to speed up the polymerization process. All the reagents were contained in 25 ml sealed flasks. The polymerization took place immediately after the addition of accelerator TEMED. The weighted percentage of the accelerator TEMED may be the reason for relatively fast polymerization. Gas was formed during the polymerization process. The poly(NIPAM) gel was immersed in DI water for over 12 hours to wash out chemical residues.

The detailed weight percentages used for the synthesis of pNIPAAm hydrogel solution described above were:
Monomer N-Isopropylacrylamide (NIPAAm): 1.5 g
Crosslinker,N,N'-methylenebisacrylamide (MBAAm): 0.0185 g
Initiator, ammonium Persulfate: 0.08 g
Accelerator: N'N,N'N'tetramethylethylenediamine: 200 μl
solvent, DI water, 50 ml Tungsten nanoparticles with an average diameter of 50 nm were purchased from NanoAmor Inc, USA; a PDMS 184 Sylgard kit, which consists of base elastomer and curing agent, was bought from Dow Corning USA. PMMA was obtained from Industrial Plastic and Paint, Surrey, Canada. All the materials were used as purchased.

In order to fabricate the tungsten nanoparticles doped microheaters, micromolds were first fabricated. The micromolds were prepared by laser ablation of cast grade PMMA (Poly Methyl Methacrylate, commercially known as Plexiglass) by using the VersaLASER© laser ablation system which employs a class 3R CO2 laser diode operating at 650 nm wavelength. The layout of the heaters was designed using Corel Draw version X4. This software is coupled to the UCP (Universal Control Panel) software which runs the VersaLASER© laser ablation system. In order to achieve a depth of 250 µm the system was operated at 100% speed and power intensity of 30%. The depth of the mold was evaluated using a micrometer.

After making the micromold, we fabricated the C-NCP heaters using soft lithography: 1.5 grams of tungsten nanoparticles with an average particle size of 50 nm were first manually stirred in 0.99 grams of PDMS base elastomer for 5 minutes. A horn tip ultrasonic probe was then immersed in the uncured composite operating at a frequency of 42 kHz in pulse mode (10 seconds on and 15 seconds off) for 30 minutes prior to adding curing agent. The base elastomer and curing agent ratio were chosen to be 10:1 respectively as recommended by the supplier (Dow Corning Inc. USA).

The prepared composite was placed into a vacuum chamber to remove air bubbles for 30 minutes and poured on to a PMMA micromold and degassed for ten minutes. Excess nanocomposite was scraped off using a Damascene-like process from the surface of the mold using a surgical knife.

Figure 5:
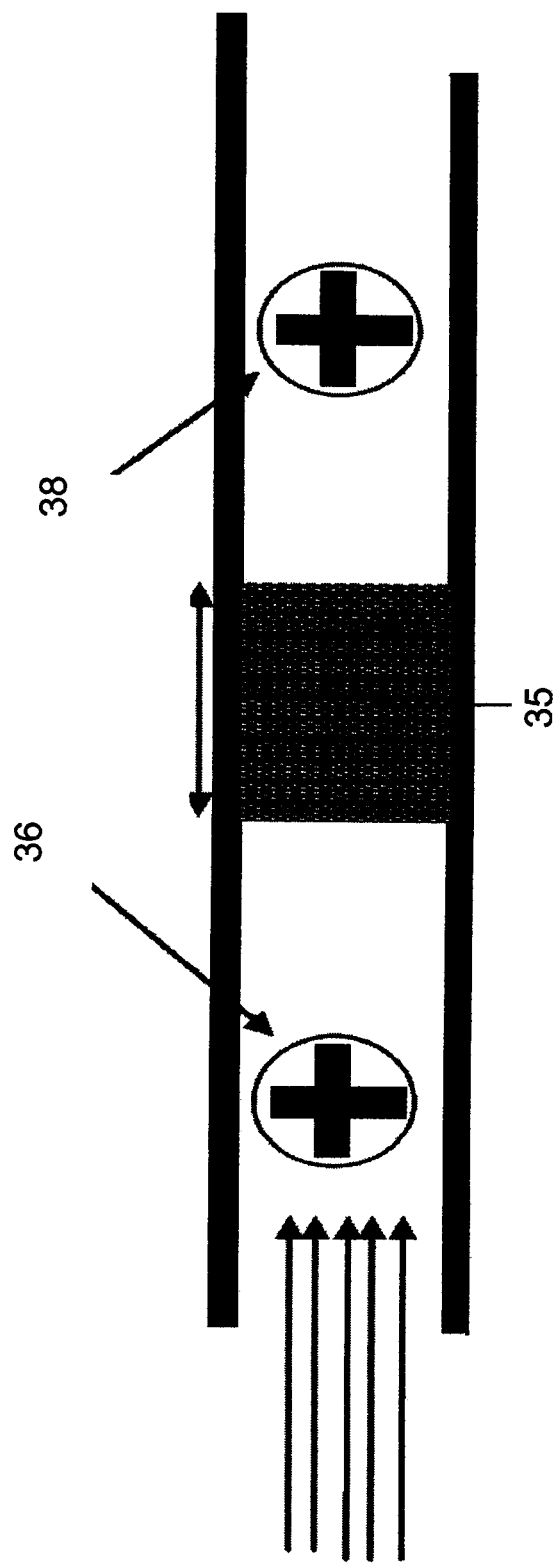
FIG. 5 illustrates the design of patterned PNIPAAm hydrogel plug of 500 μm square inserted into PDMS channel.

Undoped PDMS polymer was then poured on the surface and degassed. The substrate was then baked on a hotplate at 60° C. for 3 hours and then peeled off from the mold. FIG. 5 shows an optical micrograph of an example array of fabricated tungsten-PDMS nanocomposite microheaters.

Example 3 Fabrication of Hydrogel-Based Microvalve Actuator

Each microactuator consists of (1) a W-PDMS C-NCP flexible heater; (2) a flexible PDMS diaphragm; and (3) a reservoir of the thermally responsive hydrogel PNIPAAM. The reservoir is situated between the microheater and PDMS membrane. It could also be situated on top of the track depending on the application. Tracks could easily be added via bonding on top of the PDMS surrounding the diaphragm so that the diaphragm normally fills (and closes) the channel. The microfluidic channel could be fabricated by micromolding of poly-dimethylsiloxane (PDMS, sylgard 184) against an SU-8 or PMMA micromold.

After the polymerization of the PNIPAAM hydrogel in situ, a reservoir layer was created that ultimately fits between the actuating diaphragm and the heater. A porous, hydrophilic material was required for the temporary reservoir layer as the hydrogel expels its fluid when heating. Sponges or porous gels (e.g., Acrylamide gel, AAm) are both suitable materials for filling the reservoir layer. The reservoir layer containing the porous gel or sponge was used to stop hydrogel movement due to its relatively lower mechanical compliance, so that swelling would only occur in the upward direction.

The NCP flexible heaters, located on the bottom of the assembly, were used to provide the necessary heat for the reservoir of hydrogel and aqueous solution to regulate the movement of the thermally responsive valve actuator. After each component was individually fabricated, bonding was performed after exposure to oxygen plasma. The entire structure was assembled by clamping together all portions of the device after plasma-assisted bonding, with separation between the heater and the diaphragm by a flexible thin silicone rubber plate of 2 mm thick.

A layer of PDMS serves as the actuator diaphragm and as a barrier layer stopping the fluid from penetrating through the reservoir to the track. PDMS has the advantages of high elasticity and easy deformation under actuation. The thickness of the PDMS membrane is important so that it can be pushed out as the hydrogel swells. PDMS films with thickness less than 80 µm. In order to facilitate the desired PDMS membrane deflection of 100 µm, we calculated that a thickness of 80-150 µm would be optimal for the PDMS membrane.

For fabrication of the PDMS diaphragm, we first manually mixed 10:1 wt. ratio of PDMS prepolymer/curing agent with hexane for 1 minute which we then degassed for 1 hour. The PDMS elastomer base was Sylgard 184, which can be diluted up to 40% with hexane to adjust the viscosity and the thickness of the resulting PDMS membrane. A 3 inch diameter wafer was silanized by applying tridecafluoro-1, 1,2,2,-tetrahydrooctyl)-1-trichlorosilane for easy release of the PDMS. 2-3 ml of the PDMS/hexane mixture was dispensed with a 14 gauge needle onto the wafer using a 2-20 ml pipette and then spun the wafer using the following set of spin speeds: 500, 1000, 1500, or 2000 rpm for 30 seconds. This resulted in a PDMS film of ~100-150 µm on the wafer surface. The wafer was then heated at 85° C. for 2 hours on a hot plate to cure the PDMS film. The PDMS film was removed from the wafer by using a sharp and curved tweezers.

Example 4 Hydrogel-Based Microactuator Deflection Results

Figure 4:
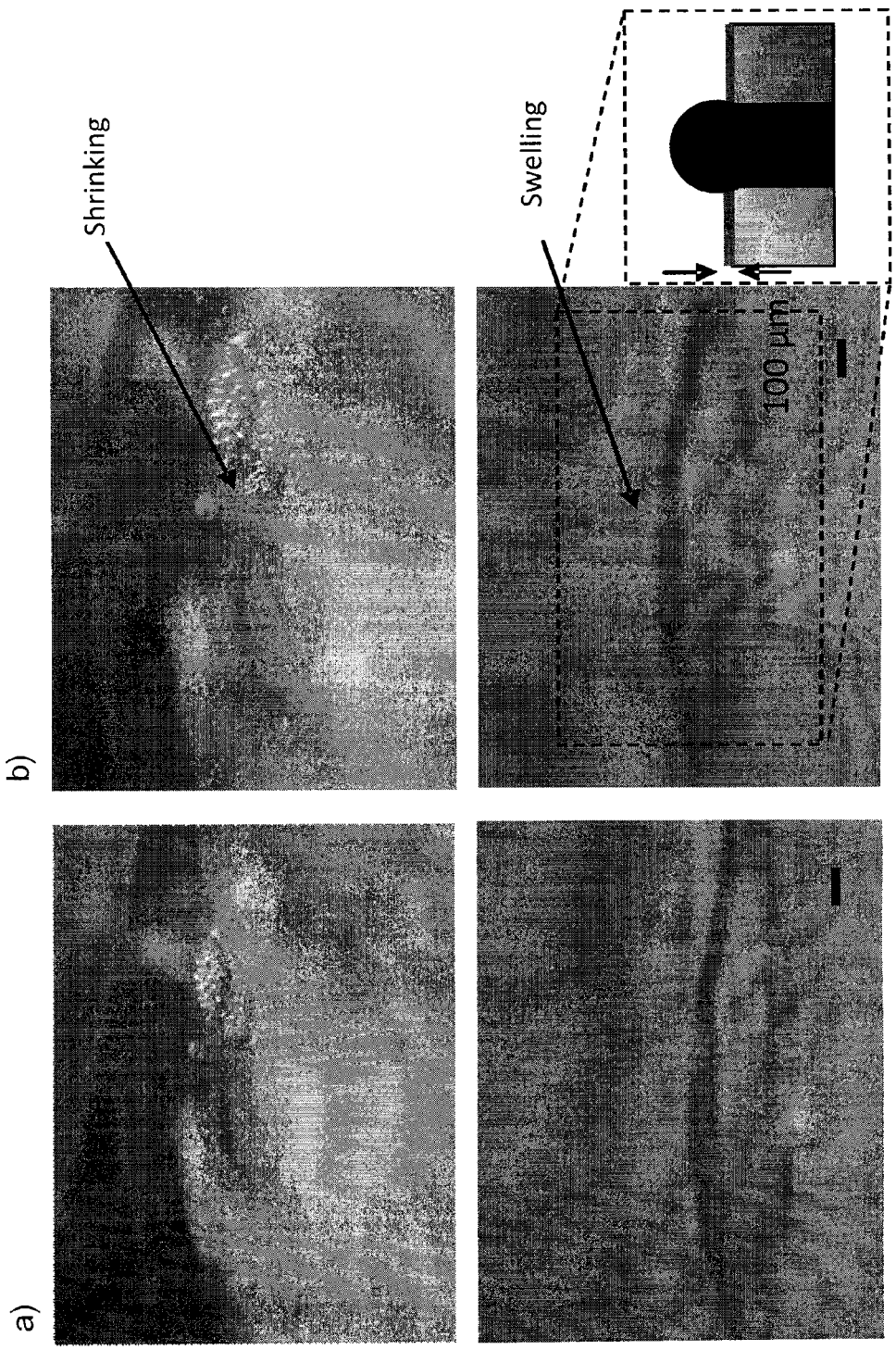
FIG. 4 is a photomicrograph of a magnetic nanocomposite polymer diaphragm microactuators suitable for use in microvalve array wherein membrane consists of 5-micron $(Nd_{0.7}Ce_{0.3})_{10.5}Fe_{83.9}B_{5.6}$ powder at 75 wt-% in PDMS polymer base.

The thermoresponsive hydrogel microvalve will be employed for control flow by opening and closing the track by blocking and unblocking the channel with a hydrogel actuated PDMS membrane (microactuator). The PDMS membrane deflection results are presented using heat supplied by the novel W-PDMS flexible heaters. The two ends of the C-NCP heaters were connected to a DC power source to control temperature. The PDMS membrane deflection images were captured using a digital camera (Canon Powershot S3-IS) mounted on a microscope (Motic SMZ-168). FIG. 4(a) illustrates the state of the PDMS membrane, which was forced to deflect downwards (in the picture) due to de-swelling of the hydrogel in response to heat from the flexible W-PDMS heater. The voltages employed for the heater element were 15-20 V. As seen in FIG. 4(a) after 30 s of heating, and in FIG. 4(b) after 1 minute of heating, the color of the hydrogel has turned to a milky white at a temperature of ~40° C. After removing the power (heat) supplied to the hydrogel, the hydrogel slowly turns from milk white to transparent (taking more than 120 s). In order to speed up the swelling process, a cold aqueous solution (10° C.) was injected with pipette (2-20 ml) into the reservoir layer. FIG. 4(c) illustrates the state of PDMS membrane after cooling/swelling, showing the convex shape due entirely to swelling of the hydrogel. The time for moving the actuator into the "open" valve position (de-swelling) was relatively faster than moving it into the "closed" valve position (swelling). Based on the times required for membrane deflection, the average time for opening a microvalve employing this membrane actuator (via de-swelling) would be 30 seconds and the average time for "closing" the valve (swelling) would be 120 seconds.

FIG. 4d PDMS membrane actuated by employing flexible W-PDMS C-NCP heater for hydrogel thermal response (membrane thickness~100 µm) (a) Hydrogel starts to shrink immediately upon the flexible microheater causing the fluid temperature to exceed the volume phase transition temperature of 32° C.; the valve was opened after 30 seconds of heating (b) the state of PDMS membrane after 1 minute of heating at 40° C. c) hydrogel was swollen by injecting a cold aqueous solution (10° C.) into the reservoir d) the state of PDMS membrane after 4 minutes of initial cooling at room temperature. Figures (c) and (d) show an estimated deflection of ~100 µm.

Example 5—Micropatterned Hydrogel Plug Structures

The 500 µm-square micropatterned hydrogel plug structures were used as fluidic control components. Two different microvalve experiments were developed employing micropatterning of the PNIPAAm hydrogel. In this first case, the PNIPAAm hydrogel was confined in polyethylene tubing of 0.58 mm inner diameter (purchased from Intramedic). In the second case, the hydrogel was simply inserted into a PDMS channel of 500 µm×500 µm×5 cm as illustrated in FIG. 5, with anchors 36 and 38 on either side to prevent the plug 35 from moving down the length of the channel. The track was fabricated using conventional soft lithography processing. Each of these designs were then affixed to the flexible heaters. The role of the temperature responsive hydrogel is to control the fluidic flow by opening and closing the tubing or track, thus acting as normally-closed in-plane valve.

Example 6 Valve Creation—Magnetic Valve

Poly(methylmethacrylate) (PMMA) sheets (ACRYLITE® FF) of 3 mm thickness were purchased from Industrial Paints and Plastics, Canada. Polydimethylsiloxane (PDMS) (Sylgard 184 Elastomer Kit), consisting of a base elastomer and curing agent, and heptane (used as a solvent for nanoparticle dispersion), were purchased from Dow Corning, USA. MQP-12-5 magnetic powder (($Nd_{0.7}Ce_{0.3})_{10.5}Fe_{83.9}B_{5.6}$) was donated by Magnequench International Inc. These materials were used as-is from the manufacturers. Compact copper coils were used for generation of controlled, external magnetic fields up to 6.5 mT. These were removed from common, magnetic, hard disk-drivers that contained 80 turns of 175 micron copper wire in an approximately square shape with side lengths of roughly 1.8 cm. Supplemental NdFeB rare earth bulk magnets were used to produce higher strength magnetic fields for further characterization.

Mold and Enclosure Fabrication

PMMA is a common polymer used in microfluidics research and commercial devices due to several factors such as low cost, biocompatibility, optical properties, and being chemically inert. PMMA also allows for low-cost rapid prototyping of many common structures in microfluidics, such as wells and microchannels. To machine the PMMA, 3 mm thick PMMA sheets (ACRYLITE® FF) were purchased from Industrial Paints and Plastics and cut and engraved using the Universal Laser System's VersaLASER© laser ablation system. This laser machining formed the enclosures and molds necessary to fabricate and characterize the microactuators. The laser is capable of cutting through PMMA thickness of over 1 cm, and was therefore sufficient for the through holes and dicing necessary for the enclosures. It can also be used to reliably etch (ablate) depths and line widths in increments of approximately 100 microns, but is able to work at resolutions as small as 20 microns with less repeatability. Squares measuring 3 inches by 3 inches cut from the PMMA sheets were used as the base structures for the nanocomposite molds. On the base structures, smaller squares of various areas were laser-ablated to depths of 500 microns to form molds for the micromagnets. Alignment marks, used to align the magnetic PDMS actuators over their enclosures, were also etched at these depths.

Magnetic Polymer and Actuator Fabrication

MQP-12-5 magnetic powder (($Nd_{0.7}Ce_{0.3})_{10.5}Fe_{83.9}B_{5.6}$) was provided (donated) by Magnequench International Inc. and is used to produce M-NCP by embedding the powder in the highly flexible polymer PDMS, thus creating a highly flexible and permanently magnetic polymer material. This approach has many advantages over other methods of producing micromagnets previously reported by other researchers, such as ferrite magnetic powders and micromachined bulked permanent magnets. Being an isotropic powder, no consideration of magnetic alignment is necessary during processing; orientation can be achieved after formation by exposure to a 2.5 T external magnetic field, meaning that the magnetic polymer can be polarized permanently in the desired direction, which can be arbitrarily set. The 5-6 micron-sized grains of the MQP-15 powder also allow for the fabrication of much smaller micromagnets as compared to bulk magnetic materials, as bulk magnets lose resistance eto demagnetization as the size approaches their internal grain sizes.

PDMS polymer was used in the binding agent (polymer matrix) for the MQP-12-5 powder to produce the M-NCP. The base elastomer and curing agent provided by Dow Corning Inc. USA were mixed by hand in a 10:1 ratio by weight as recommended by the manufacturer. The PDMS was then placed into a vacuum chamber for 30 minutes to remove any latent air bubbles (degassed). The MQP-12-5 powder was then mixed into the PDMS base manually at a weight percentage of 75 wt-%. After sufficient manual mixing, an ultrasonic horn tip probe was immersed into the composite for one hour at an operating frequency of 42 kHz. The chemical solvent heptane, provided by Dow Corning Inc. USA, was used throughout the mixing to facilitate the process and produce uniform dispersal of MQP powder in the polymer matrix. After mixing, the nanocomposite was poured over the PMMA actuator micromold. Excess nanocomposite was removed from the mold, leaving only the etched areas filled. More nanocomposite was then poured on the mold and spun at 1500 r.p.m for 30 seconds, forming a thin nanocomposite membrane 100 microns thick (FIG. 2a). The actuators were again placed in a vacuum pump for 30 minutes to remove any final air bubbles, and baked in a convection oven for 4 hours at 80° C. The actuators were then peeled from the mold and placed on the bottom enclosure fitting the alignment marks, and the top enclosure was placed above. A single actuator is shown in FIG. 2b.

Example 7—qPCR

The following is a basic process for multiple samples in multiple wells:
1. flow in reagents into well (template DNA, complementary primers (about 20 nucleotides), thermostable polymerase enzyme (e.g., TAQ), single nucleotides (A, C, G, T), MAYBE buffers (pH & ionic concentrations)), reporters, sample, and other agents specific to the desired reaction
(cleaning/blanking as needed either between loadings and/or after)
2. heat to denaturation to separate template DNA (95° C.)
3. annealing to attach primers (55° C.) at lower temperature
4. chain building in mid-range temp (72° C.) requires polymerase enzyme
5. continually or after a set number of cycles 2-3-4 monitor reporter (sense) using sensor module; DNA will double after each cycle
6. flush everything out to either another test or waste
7. cleaning/blanking step as needed For multiple *tests* on either same or multiple samples, this could be altered so that DIFFERENT things go into each well in step 1, and potentially DIFFERENT sensors are used in step 5.

The invention claimed is:

1. A reconfigurable microfluidics multiplexing device for biological and chemical sample analysis comprising:
   a) a cartridge comprising one or more sample fluid tracks, both horizontal and vertical, in a single plane;
   b) an array comprising one or more electronically programmable valves capable of being configured and reconfigured in situ during a runtime comprising a run to alter fluid steering in the one or more sample fluid tracks;
   c) a first mechanism for the array to interface with the one or more sample fluid tracks;
   d) a second mechanism that controls forward and back fluid flow dynamically in the one or more sample fluid tracks;
   e) a plurality of connections between vertical and horizontal tracks which may or may not be multi-dimensional fluidic track; and
   f) a computer, wherein the computer is programmed to direct control of the one or more electronically programmable valves via control logic within the device, wherein such control is dynamic and enables in situ reconfiguration of the one or more electronically programmable valves and the one or more sample fluid tracks during the runtime without having to stop a run, and wherein,
   valves positions of the one or more electronically programmable valves are controllable and alterable by the computer during the runtime without having to stop the run.

2. The device of claim 1 wherein the sample fluid tracks are configurable.

3. The device of claim 1 wherein a valve in the one or more electronically programmable valves is hydrogel based.

4. The device of claim 3 wherein hydrogel is polymer based.

5. The device of claim 3 wherein the hydrogel is poly(N-isopropylacrylamide) (PNIPAAm) or another thermally-responsive hydrogel.

6. The device of claim 1 wherein a first valve of the one or more electronically programmable valves is magnetic based.

7. The device of claim 6 wherein the first valve is selected from the group consisting of a nickel-based valve, an iron-based valve, and a valve made of hard magnetic particles and nanoparticles.

8. The device of claim 3 wherein the valve is capable of being configured to alter fluid steering in the fluid tracks by the application of heat.

9. The device of claim 6 wherein the first valve is capable of being configured to alter fluid steering in the fluid tracks by the application of a micromagnetic force.

10. The device of claim 1 additionally comprising one or more sensors to aid in fluid control.

11. The device of claim 10 wherein a sensor in the one or more sensors is an electro-impedance sensor.

12. The device of claim 10 wherein a sensor in one or more sensors is an optical sensor.

13. The device of claim 1 wherein the cartridge is disposable.

14. The device of claim 1 wherein the first mechanism for the array to interface with the fluid tracks is a flexible membrane or cantilever structure.

15. The device of claim 1 comprising an electronic control board.

16. The device of claim 1 comprising a display for sensor readings.

17. The device of claim 1 wherein the cartridge includes a sample solution access point.

18. The device of claim 1 which is portable.

19. The device of claim 1 wherein the device is configured to be tagged with a tag to indicate its general interconnect topology.

20. The device of claim 19 wherein the tag is an RF id tab or bar encoding.

21. The device of claim 1 which is entirely re-usable with the exception of the cartridge.

22. The device of claim 6 wherein the first valve is made of FeC, CoFe, CoFeZn, $Ni_{0.5}Co_{0.5}Fe_2O_4$, $Zn_{0.5}Co_{0.5}Fe_2O_4$, $Zn_{0.5}Ni_{0.5}F$, NdFeB, $CoFe_2O_4$, $NiFe_2O_4$, $ZnFe_2O_4$, $Ni_{0.5}Co_{0.5}Fe_2O_4$, $Zn_{0.5}Co_{0.5}Fe_2O_4$, $Zn_{0.5}Ni_{0.5}Fe$, $SrFe_{12}O_{19}$, MQFP or combinations thereof.

23. The device of claim 10 wherein
   the one or more sensors produces a sensor output, and
   the one or more electronically programmable valves are reconfigured during the runtime based upon the sensor output from the one or more sensors by the computer.

24. The device of claim 1 wherein the computer comprises a user interface, and wherein the one or more electronically programmable valves are controllable and alterable by the computer via the user interface.

* * * * *